US010308990B2

(12) United States Patent
Patterson et al.

(10) Patent No.: US 10,308,990 B2
(45) Date of Patent: Jun. 4, 2019

(54) METHODS OF EVALUATING A CELLULAR SAMPLE FOR LATENT CELLULAR REPLICATION COMPETENT HIV-1

(71) Applicant: IncellDx, Inc., Menlo Park, CA (US)

(72) Inventors: Bruce K. Patterson, Palo Alto, CA (US); Amanda Noel Chargin, San Jose, CA (US); Fangfang Yin, Palo Alto, CA (US); Min Song, Redwood City, CA (US); Srividyabhuvaneswari Subramaniam, Chennai (IN); Grace Elaine Knutson, Menlo Park, CA (US)

(73) Assignee: IncellDx, Inc., San Carlos, CA (US)

( * ) Notice: Subject to any disclaimer, the term of this patent is extended or adjusted under 35 U.S.C. 154(b) by 0 days.

(21) Appl. No.: 14/807,817

(22) Filed: Jul. 23, 2015

(65) Prior Publication Data

US 2016/0024602 A1 Jan. 28, 2016

Related U.S. Application Data (60) Provisional application No. 62/029,394, filed on Jul. 25, 2014.

(51) Int. Cl.
*C12Q 1/70* (2006.01)
*C12M 1/24* (2006.01)

(52) U.S. Cl.
CPC ............. *C12Q 1/703* (2013.01); *C12M 23/08* (2013.01)

(58) Field of Classification Search
None
See application file for complete search history.

(56) References Cited

U.S. PATENT DOCUMENTS

| | | | |
|---|---|---|---|
| 6,235,304 B1 | 5/2001 | Patterson | |
| 6,329,152 B1 | 12/2001 | Patterson | |
| 6,329,167 B1 | 12/2001 | Patterson | |
| 6,582,901 B2 | 6/2003 | Patterson | |
| 7,524,631 B2 | 4/2009 | Patterson | |
| 2001/0039007 A1 | 11/2001 | Hallowitz et al. | |
| 2011/0111981 A1 | 5/2011 | Love et al. | |
| 2012/0122078 A1 | 5/2012 | Patterson | |
| 2014/0065601 A1 | 3/2014 | Jehuda-Cohen | |
| 2014/0199722 A1 | 7/2014 | Patterson | |
| 2014/0308658 A1* | 10/2014 | Kay | C12Q 1/06 435/5 |

FOREIGN PATENT DOCUMENTS

| | | | |
|---|---|---|---|
| CN | 101890189 A | | 11/2010 |
| WO | WO 1993/11435 | * | 6/1993 |
| WO | WO2007121429 A2 | | 10/2007 |

OTHER PUBLICATIONS

Hermankova et al., Journal of Virology, 2003, 77(13):7383-7392.*
Gunthard et al., Journal of Virology, 1998, 72(3):2422-2428.*
Lambotte et al., JAIDS Journal of Acquired Immune Deficiency Syndrome, 2000, 23:114-119.*
Ai et al., Int. J. Environ. Res. Public Health, Aug. 2013, 10:3834-3842.*
Deenadayalan et al., BMC Research Notes, 2013, 6:120.*

* cited by examiner

*Primary Examiner* — Nicole Kinsey White
(74) *Attorney, Agent, or Firm* — Otto C. Guedelhoefer, IV; Bret E. Field; Bozicevic, Field & Francis LLP (57) ABSTRACT

Methods of evaluating a cellular sample for latent cellular replication competent HIV-1 are provided. Aspects of the methods include contacting a cellular sample with an HIV-1 inducing compound to produce an activated cellular sample; and assessing plasma viral load in the activated cellular sample to evaluate the cellular sample for latent cellular replication competent HIV-1. Also provided are devices and kits that find use in practicing the methods.

21 Claims, 4 Drawing Sheets

| Patient | Drug Class Resistance Interpretation | | No. Mutations Detected in ViroSeq not found in EDTA |
|---|---|---|---|
| | Plasma (EDTA) | Plasma (ViroSeq™) | |
| 4318 | No Evidence of Resistance | No Evidence of Resistance | 5 |
| 70146 | Stavudine (d4T) Possible Resistance<br>Tenofovir (TDF) Possible Resistance<br>Zidovudine (AZT) Resistance<br>Abacavir (ABC) Possible Resistance<br>Didanosine (ddI) Resistance<br>Atazanavir (ATV) Resistance<br>ATV/r** Resistance<br>Darunavir + Ritonavir (DRV/r) Possible Resistance<br>Fosamprenavir (FPV) Resistance<br>FPV/r** Resistance<br>Indinavir (IDV) Resistance<br>IDV/r** Possible Resistance<br>Lopinavir + Ritonavir (LPV/r) Possible Resistance<br>Nelfinavir (NFV) Possible Resistance<br>Saquinavir + Ritonavir (SQV/r) Possible Resistance | Stavudine (d4T) Possible Resistance<br>Tenofovir (TDF) Possible Resistance<br>Zidovudine (AZT) Resistance<br>Abacavir (ABC) Possible Resistance<br>Didanosine (ddI) Resistance<br>Atazanavir (ATV) Resistance<br>ATV/r** Resistance<br>Darunavir + Ritonavir (DRV/r) Possible Resistance<br>Fosamprenavir (FPV) Resistance<br>FPV/r** Resistance<br>Indinavir (IDV) Resistance<br>IDV/r** Resistance<br>Lopinavir + Ritonavir (LPV/r) Possible Resistance<br>Nelfinavir (NFV) Possible Resistance<br>Saquinavir + Ritonavir (SQV/r) Possible Resistance<br>Tipranavir + Ritonavir (TPV/r) Possible Resistance | 22 |
| 11986 | Abacavir (ABC) Resistance<br>Didanosine (ddI) Resistance<br>Lamivudine (3TC) / Emtricitabine (FTC) Resistance<br>Efavirenz (EFV) Resistance<br>Etravirine (ETR) Possible Resistance<br>Nevirapine (NVP) Resistance | Abacavir (ABC) Resistance<br>Didanosine (ddI) Resistance<br>Lamivudine (3TC) / Emtricitabine (FTC) Resistance<br>Efavirenz (EFV) Resistance<br>Etravirine (ETR) Resistance<br>Nevirapine (NVP) Resistance | 4 |
| 72893 | Lamivudine (3TC) / Emtricitabine (FTC) Resistance<br>Efavirenz (EFV) Resistance<br>Etravirine (ETR) Possible Resistance<br>Nevirapine (NVP) Resistance | Lamivudine (3TC) / Emtricitabine (FTC) Resistance<br>Efavirenz (EFV) Resistance<br>Etravirine (ETR) Possible Resistance<br>Nevirapine (NVP) Resistance<br>Rilpivirine (RPV) Resistance | 9 |
| 4963 | No Evidence of Resistance | Atazanavir (ATV) Resistance<br>ATV/r** Possible Resistance<br>Nelfinavir (NFV) Resistance | 26 |
| 2119 | No Evidence of Resistance | No Evidence of Resistance | 25 |
| 11657 | No Evidence of Resistance | No Evidence of Resistance | 19 |

METHODS OF EVALUATING A CELLULAR SAMPLE FOR LATENT CELLULAR REPLICATION COMPETENT HIV-1

CROSS-REFERENCE TO RELATED APPLICATIONS

This application claims priority to U.S. Provisional Patent Application Ser. No. 62/029,394, filed on Jul. 25, 2014, the disclosure of which is incorporated herein by reference.

INTRODUCTION

The hallmark of anti-retroviral drug monitoring in HIV-1-infected individuals has been plasma viral load and CD4 counts. The utilization of combination antiretroviral therapy for HIV-1 infection has generated interest in mechanisms by which the virus can persist in the body despite the presence of drugs that are designed to inhibit key steps in the virus life cycle including infection of new cells. Viral reservoirs established early in the infection represent a major obstacle to the efficacy of antiretroviral drugs currently in use. In peripheral blood, a significant proportion of peripheral blood mononuclear cells (PBMCs) contain HIV-1 DNA. However, very few HIV-1 DNA positive PBMCs can be reactivated to express viral mRNA, implying that only a small fraction of cells in the peripheral blood are transcriptionally active and considered "active reservoirs". Peripheral blood mononuclear cells (PBMCs) and tissues such as lymph nodes respond with similar decay kinetics on antiretroviral therapy (ART), suggesting that PBMCs are an important surrogate for HIV in lymphoid tissue reservoirs.

Recently, basic science and commercial laboratories have developed tests designed to detect and/or quantify cell-associated (CA), integrated HIV proviral DNA, as well as unintegrated (episomal) HIV DNA. Though useful to estimate the total viral burden in individuals, these assays lack the ability to determine the replication competence of the HIV DNA residing in cells. Further, plasma may not be the best source of virus for anti-retroviral resistance testing as plasma virus consists of defective, non-replication competent virus in addition to replication competent HIV. In addition, studies have shown that different reservoirs of HIV in an individual may exhibit different genotypic resistance determinants; a finding that could significantly alter the choice of anti-retroviral drugs to be used in tailoring ART in HIV-1-infected individuals, especially with eradication strategies in mind that focus on inducing the replication competent latently infected cells to produce virus.

SUMMARY

Methods of evaluating a cellular sample for latent cellular replication competent HIV-1 are provided. Aspects of the methods include contacting a cellular sample with an HIV-1 inducing compound to produce an activated cellular sample; and assessing plasma viral load in the activated cellular sample to evaluate the cellular sample for latent cellular replication competent HIV-1. Also provided are devices and kits that find use in practicing the methods.

Aspects of the invention provide a diagnostic system that quantifies and characterizes the replication competent HIV-1 reservoir and permits anti-retroviral resistance testing to be performed on a broad representation of an HIV-infected individual's quasi-species.

DETAILED DESCRIPTION

Methods of evaluating a cellular sample for latent cellular replication competent HIV-1 are provided. Aspects of the methods include contacting a cellular sample with an HIV-1 inducing compound to produce an activated cellular sample; and assessing plasma viral load in the activated cellular sample to evaluate the cellular sample for latent cellular replication competent HIV-1. Also provided are devices and kits that find use in practicing the methods.

Before the present invention is described in greater detail, it is to be understood that methods, devices and kits provided herein are not limited to particular embodiments described, as such may, of course, vary. It is also to be understood that the terminology used herein is for the purpose of describing particular embodiments only, and is not intended to be limiting, since the scope of will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features, which are, for clarity, described in the context of separate embodiments, may also be provided in combination in a single embodiment. Conversely, various features, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present invention and are disclosed herein just as if each and every such sub-combination of chemical groups was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing embodiments, aspects of embodiments of the methods will be described first in greater detail. Next, embodiments of devices and kits that may be used in practicing methods provided herein are reviewed.

Methods

As summarized above, methods of evaluating a cellular sample for latent cellular replication competent HIV-1 are provided. By evaluating a cellular sample for latent cellular replication competent HIV-1 is meant assaying a physiological sample that includes a plurality of cells for the presence of dormant HIV-1 genomic DNA present in cells of the cellular sample, such as chromosomally integrated HIV-1 genomic DNA, which genomic DNA can be transcribed to ultimately give rise to mature HIV-1 viral particles. Assaying for the presence of such HIV-1 genomic DNA may include a qualitative or quantitative determination, as desired.

The cellular sample that is assayed in methods of the invention may vary. The cellular sample may be obtained from any convenient source. In certain embodiments, the sample is one that is obtained from a "mammal" or "mammalian subject", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, subjects are humans. The term "humans" may include human subjects of both genders and at any stage of development (e.g., fetal, neonates, infant, juvenile, adolescent, adult), where in certain embodiments the human subject is a juvenile, adolescent or adult.

The cellular sample may be a blood sample. The blood sample may be whole blood or a faction thereof, as desired. In some instances, the sample is a whole blood sample. As used herein, "whole blood" refers to blood from which no constituent, such as red blood cells, white blood cells, plasma, or platelets, has been removed. Whole blood sample refers to a sample of whole blood collected from a subject. The terms "subject", "individual", and "patient" are used herein interchangeably to refer to the subject from whom whole blood sample has been obtained.

Where the sample is a blood sample, the methods may be methods of evaluating latent cellular replication competent HIV-1 that is present in peripheral blood mononucleated cells (PBMCs). As such, the methods may be methods of evaluating cellular replication competent HIV-1 in blood cells having a round nucleus, such as one or more of lymphocytes (e.g., T cells, B cells and NK cells), monocytes and macrophages, etc. Aspects of the methods include contacting the sample, e.g., whole blood sample, with an HIV-1 inducing compound. By HIV-1 inducing compound is meant an agent that stimulates a cell in a manner such that latent virus present in the cell, e.g., as integrated genomic DNA, is activated to produce viral particles. As such, the agent is one that stimulates dormant viral genomic DNA into an active state, thereby providing for virus production. In other words, the substance used to induce active viral replication is generally a substance which induces the activation or proliferation of the latently infected cell or is a substance capable of inducing viral replication. The HIV-1 inducing agent may vary. Examples of HIV-1 inducing agents of interest include, but are not limited to: mitogenic lectins, such as phytohemagglutinins; polyclonal or monoclonal antibodies capable of binding T cell surface molecules such as, e.g., $\alpha$, $\beta$, $\gamma$ or $\delta$ T cell receptors, CD3, CD2, CD4, CD8, CD2B, Thy-1, etc.; bispecific monoclonal antibodies capable of binding more than one antigen, e.g., a bispecific monoclonal antibody (BSMAB) having specificity for both CD3 and CD8, (CD3,8 BSMAB) etc. As such, HIV-1 inducing compounds of interest include lectins, e.g., phytohemagglutinin (PHA) (Hermankova et al., 2003 J Virol, 77 (13), 7383-7392); antibodies, e.g., cross-linking anti-CD3 antibodies (Wong et al., 1997 Science, 278 (5341), 1291-1295); and the like. Also of interest are substances that can activate viral replication directly, which substances may include: cytokines, such as TNF-$\alpha$ and other stimulators of NF$\kappa$B activity, analogs or fragments of cytokines such as IL-1 and IL-2 and IL-7, and transactivators encoded by various sequences from various virus, e.g., herpes virus (HSV, EBV, CMV, HHV-6), HTLV-1, and HBV.

The amount of HIV-1 inducing agent that is contacted with the sample may vary, e.g., depending on the sample, depending on the agent, etc., where the amount may be any amount sufficient to provide for the desired induction of active replication from previously latent genomic viral DNA.

The sample and HIV-1 inducing agent may be combined using any convenient protocol. For example, the method may include placing an amount of the HIV-1 inducing agent in a volume of the sample. Alternatively, the method may include placing an amount of sample into a container that includes an amount of HIV-1 inducing agent. As such, embodiments of the methods include using a container that includes the HIV-1 inducing agent present therein, e.g., as described in greater detail below. The container for processing the whole blood sample may be a container that includes a HIV-1 inducing agent. The HIV-1 inducing agent may be disposed in the container prior to or after the sample, e.g., whole blood sample, is added to the container. In certain cases, the whole blood sample may be collected in a container and the HIV-1 inducing agent may be added to that container to initiate the desired replication of any latent virus of the cells in the sample. The HIV-1 inducing agent may be added to that container within 12 hours of collecting the whole blood sample. For example, the HIV-1 inducing agent may be added to that container within 10 hours, 8 hours, 6 hours, 4 hours, 2 hours, 1 hours, 30 min, 20 min, 10 min, 5 min, or 1 min of collecting the whole blood sample. In certain cases, the whole blood sample may be collected in a container in which the HIV-1 inducing agent is disposed. For example, the container may include a coating or a suspension of the HIV-1 inducing agent. In this case, the adding of the whole blood sample leads to the activation of the latent virus. Aspects of the present methods include the use of an evacuated container, as described in the section below, for the collection and virus activation steps. In this aspect, the whole blood sample may be collected into the evacuated container which includes an HIV-1 inducing agent, e.g., as described above.

In certain embodiments, a container containing the HIV-1 inducing agent and the sample may be rotated, rocked, or shaken to facilitate the interaction of the sample with the inducing agent. As such, a container containing the HIV-1 inducing agent and the sample may be incubated by rotating, rocking, or shaking for a desired period of time, e.g., 5 min to about 5 hours, at any convenient temperature, e.g., 1 to 40° C., including room temperature, to facilitate the interaction of the sample with the inducing agent.

Generally, contacting the sample with the HIV inducing agent occurs outside the subject or in vitro. As such, the sample and the HIV inducing agent are contacted in a suitable container, as described above, after the sample is collected from a subject. Accordingly, in some instances, the sample is collected from a subject that is essentially free of pharmacologically administered HIV inducing agent. In such instances, the subject has not been administered the HIV inducing agent or, in a subject that has previously been administered an HIV inducing agent, the HIV inducing agent is no present or longer biologically active.

The evaluations described herein do not necessarily require that cells of the cellular sample be cultured in order to facilitate the activation of latent HIV with an HIV inducing agent. By "cultured", as used here, is meant that the cells are contacted with culture medium (e.g., growth medium) and/or a cell culture agent (e.g., a growth factor or differentiation factor) such that the cells grow, proliferate and/or differentiate. In some instances, the method is performed essentially without culturing the cells of the cellular sample. In some instances, the method is performed essentially without contacting the cellular sample with cell culture medium. Where an HIV inducing agent may be considered a growth factor or differentiation factor and is utilized in the method as an HIV inducing agent the growth factor or differentiation factor is not included in the definition of a "cell culture agent" as used herein.

In some instances, following contacting the sample with the HIV-1 inducing agent in a suitable container, the container may be incubated under conditions suitable for virus production in any stimulated replication competent latently infected cells that may be present in the sample. For example, the container may be incubated at a permissive temperature for virus production including but not limited to a temperature ranging from less than 35° C., but generally more than about 34° C., to more than 39° C., but generally less than about 40° C., including but not limited to, e.g., from 34.0° C. to 40.0° C., from 34.5° C. to 39.5° C., from 35.0° C. to 39.0° C., from 35.5° C. to 38.5° C., from 36.0° C. to 38.0° C., from 36.5° C. to 38.5° C., from 36.5° C. to 38.0° C., from 36.5° C. to 37.5° C., etc. Incubation may be performed in any suitable incubator including but not limited to, e.g., a water bath, a heat block, etc.

Incubation under conditions suitable for virus production will vary and may be maintained for any convenient amount of time where the length of incubation may depend upon the sensitivity of the virus detection assay utilized in downstream steps, the desired speed of performing the overall evaluation, and the rate of virus production in stimulated cells. For example, where a highly sensitive virus detection assay is utilized, incubation time may be shorter than the incubation time necessary when the method is performed with a less sensitive virus detection assay. In instances where rapid detection is not a priority, a longer incubation time may be utilized as compared to when rapid detection is desired.

As such, in some instances, incubation under conditions suitable for virus production may be performed for a length of time ranging from less than 24 hours but generally more than 12 hours to more than 72 hours but generally less than 96 hours, including but not limited to, e.g., from 12 hours to 96 hours, from 12 hours to 84 hours, from 12 hours to 72 hours, from 12 hours to 60 hours, from 12 hours to 48 hours, from 12 hours to 36 hours, from 12 hours to 24 hours, from 18 hours to 96 hours, from 18 hours to 84 hours, from 18 hours to 72 hours, from 18 hours to 60 hours, from 18 hours to 48 hours, from 18 hours to 36 hours, from 18 hours to 24 hours, from 24 hours to 96 hours, from 24 hours to 84 hours, from 24 hours to 72 hours, from 24 hours to 60 hours, from 24 hours to 48 hours, from 24 hours to 36 hours, from 36 hours to 96 hours, from 36 hours to 84 hours, from 36 hours to 72 hours, from 36 hours to 60 hours, from 36 hours to 48 hours, from 42 hours to 52 hours, etc.

In some instances, the length of incubation may be chosen such that the overall duration of the method of evaluating the sample (e.g., from sample collection through vial load assessment) is performed in less than 3 days including but not limited to, e.g., less than 2.5 days or less than 2 days.

Cellular samples that may be evaluated according to the methods as described herein may be processed by various means either before or after contacting the sample with an HIV inducing agent. For example, in some instances a whole blood sample may be contacted with an HIV inducing agent prior to processing, e.g., following collection where no processing steps are performed between collection of the sample and contacting the sample with the HIV inducing agent. In such instances, following contacting the sample with the HIV inducing agent, and any subsequent incubation, the sample may be further processed. In other instances, a whole blood sample may be processed after collection but before contacting the sample with an HIV inducing agent.

Cellular sample processing steps that may find use in the subject methods, including automated processing steps, will vary depending on the goal of the evaluation and the particular assessments made. In some instances, a cellular sample may be processed by fractionation where the sample is subdivided into one or more of its component parts including but not limited to, plasma, cellular fraction (e.g., white blood cells and platelets), red blood cell fraction. In some instances, fractions may be collected together, e.g., plasma may be collected with the cellular fraction. In some instances, a physical separation method may be employed to fractionate a cellular sample where any convenient method of physical separation may find use processing the sample including but not limited to, e.g., the use of a gel plug that separates the plasma from the cells when centrifuged. In other instances, a cellular sample may be processed by lysing a particular cell population of the sample, e.g., lysing the red blood cells of the sample.

In some instances, a cellular sample may be processed by isolating a particular subpopulation of cells for further treatment and/or analysis. For example, a particular subpopulation of white blood cells may be isolated including but not limited to a neutrophil subpopulation, a monocyte subpopulation, a lymphocyte subpopulation, an eosinophil subpopulation or a basophil subpopulation. In some instances, a subpopulation of white blood cells may be isolated based on its expression of one or more cell surface markers including but not limited to e.g., one or more human CD antigens including those CD antigens described in Janeway et al. *Immunobiology: The Immune System in Health and Disease.* 5th edition. New York: Garland Science. 2001; the disclosure of which is incorporated herein by reference in its entirety. In some instances, a combination of two or more cell surface markers may be used to define and/or isolate a subpopulation of the cellular sample including but not limited to e.g., co-expression of CD3 and CD4. Any convenient means of detecting surface marker expression and isolating cell subpopulations based on surface marker expression may be utilized including but not limited to, e.g., affinity based-isolation, magnetic cell separation, fluorescence activated cell sorting (FACS), etc. Isolated subpopulations of a cellular sample may be independently analyzed, e.g., independently assessed to determine viral load of the subpopulation, independently assessed to determine the genotype of activatable virus of the subpopulation, etc.

Following contacting with an HIV inducing agent for a suitable incubation period, with or without further sample processing steps, the resultant activated cellular sample is assayed to determine viral load in the HIV-1 activated cellular sample. The term "viral load" is employed in its conventional sense to refer to the amount of HIV-1 in the sample. Viral load, also known as viral burden, viral titre or viral titer, is a measure of the severity of a viral infection, and can be calculated by estimating the amount of virus in an involved body fluid. In some instances, the viral load is provided in RNA copies per milliliter of blood plasma.

Any convenient protocol for determining viral load in the activated cellular sample may be employed. In some instances a fraction of the activated cellular sample is assayed for viral load. The fraction may vary, and in some instances the fraction is a blood plasma fraction. By plasma fraction is meant the portion of blood that the clear yellowish fluid portion of the blood or lymph in which the red blood cells, white blood cells, and platelets are suspended. The plasma fraction may be obtained from the activated cellular sample using any convenient protocol, e.g., centrifugation, centrifugation coupled with physical separation, apheresis, etc.

In some instances, a nucleic acid mediated protocol is employed to determine viral load. By nucleic acid mediated protocol is a meant a protocol that employs the detection of HIV-1 nucleic acids in the sample to determine of viral load. Nucleic acid mediated protocols may detect the RNA viral genome or a portion thereof, expressed viral mRNA or a portion thereof, and/or integrated proviral DNA. In many instances, viral load is assessed by measuring viral RNA which may include both the RNA viral genome and expressed viral mRNA or may be an independent measure of the RNA viral genome or expressed viral mRNA.

Nucleic acid mediated detection protocols of interest may employ nucleic acid primers in nucleic acid amplification protocols to produce amplicons, which in turn may be detected and employed to determine viral load. The process for amplification of a desired nucleic acid sequence can be achieved by any means necessary to achieve amplification of the desired amplicon. The amplification can be achieved using any known means in the art, including polymerase chain reaction techniques. The primers and probes can be purchased or prepared by any means known in the art, including automated processes. In some instances, the primers and probes are designed for specificity for the target nucleic acid sequence, e.g., a target HIV-1 nucleic acid, e.g., gag, pol, gag-pol, env, tat, rev, nef, vif, vpr, vpu, vpx, HIV LTR, etc. The enzymes used to promote amplification can be purchased or can be prepared by any means known in the art, including cellular extraction. Substrates to aid in the amplification can also be purchased or can be prepared by any means known in the art, including any synthetic methodology to synthesize natural and unnatural nucleic acids. The enzyme and substrates can be added to the amplification mixture at any time and in any order that allows for the amplification of the desired amplicon.

Primers and probes useful in HIV detection may be modified, including synthetic modification, where such modification is required for performing a particular detection assay or improves the efficiency of the assay as compared to performing the assay without the modification. For example, probes may be labeled with a reporter (e.g., a dye), as described in more detail below. Primer and probe modifications will vary depending on the particular assay performed and may include but are not limited to e.g., 2-aminopurine modification, 2,6-diaminopurine (2-amino-dA) modification, 5-bromo dU modification, deoxy-uridine modification, inverted dT modification, inverted dideoxy-T modification, dideoxy-C modification, 5-methyl dC modification, deoxy-inosine modification, 5-hydroxybutynl-2'-deoxyuridine modification, 8-aza-7-deazaguanosine modification, C3'-endo modification (e.g., locked nucleic acid (LNA) modification), 5-nitroindole modification, 2'-O-Methyl modification, acyclic RNA modification (e.g., unlocked nucleic acid (UNA) modification, Iso-dG modification, Iso-dC modification, fluoro (e.g., fluoro-C, fluoro-U, fluoro-A, fluoro-G) modification, peptide nucleic acid (PNA) modification, morpholino modification (e.g., phosphorodiamidate morpholino modification), and the like.

Viral load measurements may be performed including or excluding viral analyte present in the cells of the cellular sample at the time of sample collection. Likewise, viral load measurements may be performed including or excluding viral analyte present outside the cells of the cellular sample at the time of sample collection. For example, in some instances, viral load including the virus within the cells at the time the sample is collected and virus outside the cells is measured, e.g., by lysing the cells of the cellular sample. In other instances, only viral load within the cells at the time the sample was collected is measured, e.g., by first washing the collected cellular sample (e.g., with an appropriate wash buffer) to remove any cell-free virus from the sample prior to the assay and/or detecting the virus in situ (i.e., inside the cell).

In some instances, viral load of stimulated cells is preferentially measured, e.g., by washing the cellular sample to remove cell-free virus and collecting virus generated following the stimulation of the cells. The virus produced following stimulation may be measured outside the cell, e.g., by measuring virus in solution following stimulation, or may be measured inside the cell, e.g., by measuring virus in situ or lysing the cells to release the virus. Measurement of viral load of stimulated cells need not, in all cases, be necessarily performed in the absence of cell-free virus present before stimulation and may, in some instances, include cell-free virus present before stimulation of the cells.

Additionally, amplification conditions of amplification mediated viral load assays will vary depending on the choice of primers and probes, due to differences in their melting temperatures (TM). Temperatures of interest range from 50° C. to 95° C. for incubation and 60° C. to 95° C. for amplification. The temperature for amplification may be any temperature that allows for replication of the desired amplicon at a suitable rate. As an exemplary embodiment, reverse-transcriptase polymerase chain reaction ("RT-PCT") can be used to amplify the desired amplicon. After reverse transcription incubation, an amplification cycle can be performed. The incubation cycle can be performed at one temperature or on a multi-temperature basis; for example, the incubation cycle can be performed on a two-step temperature gradient, e.g., first a moderate time at moderate temperature followed by an extended period at higher temperatures. The amplification cycle can be performed at one temperature or on a multi-temperature basis; for example, the amplification cycle can be performed on a two-step gradient, e.g., first a short phase of higher temperatures followed by a longer period of moderate temperatures. The amplification procedure can be repeated as many times as necessary, where 40 cycles are generally sufficient to produce sufficient amplicon for downstream steps.

The presence of the amplicon can be detected in real time based on the labeled oligonucleotide, which is labeled with a variety of substances, termed reporting dyes, and quenching dye, which upon amplification, are capable of emitting a detectable signal. Any combination of reporting dyes and quenching dyes can be used. Some non-limiting examples of reporting dyes are FAM, VIC, PAT and JOE. A non-limiting example of quenching dyes is TAMRA. These reporting dyes and quenching dyes can be purchased or can be prepared by any means known in the art, including radical and organometallic chemistry. In one embodiment, the detectable signal is a fluorescent dye that can be detected in a spectrometer that is covalently bound to a quenching dye through the oligonucleotide. This renders the fluorescent dye inactive while bound to the oligonucleotide. However, upon exonuclease degradation of the oligonucleotide, the fluorescent dye can be released from the quenching dye, thus emitting a detectable signal. Many of the new DNA tags and labels depend on two phenomena that are extensions of fluorescence: quenching and energy transfer. In general, anything that reduces the lifetime of the excited state decreases the quantum yield of the fluorophore; anything that decreases the quantum yield is called quenching. There are three main mechanisms for determining these phenomena: collisional, in which the excited state of the fluorophore loses its energy by bumping into a nonfluorescent molecule; static, in which the excited state reacts with the quencher, forming a nonfluorescent complex; and energy transfer, which involves the nonradiative transfer of energy from a donor to an acceptor.

The brightness of a fluorescent dye depends on many parameters. The parameters can be divided between the physical and chemical properties of the dyes and the excitation system. The important physical properties of the dyes are quantum yield and extinction coefficient. The quantum yield is an expression of the number of photons emitted divided by the number of photons absorbed. A quantum yield of 0 indicates a nonfluorescent molecule, and a quantum yield of 1 indicates that 100 percent of the excitation photons result in lower-wavelength emitted photons. The extinction coefficient is an expression of the probability that a photon of a given wavelength will be absorbed by the fluorophore. A high extinction coefficient combined with a high quantum yield generally leads to a "bright" fluorophore; fluorescein, for example, is a relatively "bright" dye, having an extinction coefficient of about 80,000 at its absorption maximum and a quantum yield of about 0.9.

For fluorescence resonant energy transfer (FRET) to occur, there must be a precise overlap in quantum energy levels between the donor and the acceptor, the energy being transferred by dipolar coupling rather than emission and reabsorption of a photon. FRET has been used very productively to create dyes for DNA sequencing, where a common donor eliminates the need for multiple excitation wavelengths but instead transfers its energy to four separate dyes that have easily discernable emission spectra. FRET and fluorescence quenching are very distance dependent, allowing their exploitation in several novel assays that alter donor-acceptor geometries.

Methods as described herein may depend on a variety of modified oligonucleotides. Many fluorescent dyes are available as dye-phosphoramidites (or as dye-CPG derivatives), which are compatible with automated oligonucleotide synthesis methods. Using this approach, dyes can be incorporated at the 5' or 3' end or at any internal position during routine synthesis. Similarly, amino-modified bases can be incorporated into an oligo at any position, enabling a wider variety of labeling, because many additional dyes are available in an NHS-ester form that can be conjugated to an amino-modified oligonucleotide after synthesis. Different applications call for different modifications, including such esoterica as variable-length spacers, universal bases and branched backbones.

In some instances, a quantitative real-time polymerase chain reaction protocol is employed for detection and determination of viral load. For example, quantitative real-time polymerase chain reaction using TaqMan provides an accurate method for determination of levels of specific DNA and RNA sequences in samples. It is based on detection of a fluorescent signal produced proportionally during amplification of a PCR product. Quantitative real-time PCR is based on detection of a fluorescent signal produced proportionally during the amplification of a PCR product. In such instances, a probe may be designed to anneal to the target sequence between the traditional forward and reverse primers. The probe is labeled at the 5' end with a reporter fluorochrome (usually 6-carboxyfluorescein [6-FAM]) and a quencher fluorochrome (6-carboxy-tetramethyl-rhodamine [TAMRA]) added at any T position or at the 3' end. The probe is designed to have a higher Tm than the primers, and during the extension phase, the probe must be 100% hybridized for success of the assay. As long as both fluorochromes are on the probe, the quencher molecule stops all fluorescence by the reporter. However, as Taq polymerase extends the primer, the intrinsic 5' to 3' nuclease activity of Taq degrades the probe, releasing the reporter fluorochrome. The amount of fluorescence released during the amplification cycle is proportional to the amount of product generated in each cycle.

Nucleic acid mediated viral load assays finding use in methods of invention include, but are not limited to, those described in U.S. Published Patent Application Nos. 20120135397; 20100124744; 20100015598; 20070196824. Commercially available nucleic acid mediated viral load detection assays include, but are not limited to: the Roche (Branchburg, N.J.) Cobas AmpliPrep/Cobas TaqMan (CAP/CTM) HIV-1 viral load assay; the Abbott Molecular (Des Plaines, Ill.) RealTime HIV-1 viral load assay; the NucliSens HIV-1 QT (bioMerieux, Durham N.C.); etc.

In some embodiments, the method further includes genotyping identified latent cellular replication competent HIV-1. Any convenient protocol may be employed to genotype the latent cellular replication competent HIV-1 of the sample. In some instances, amplicons produced in the viral load assay may be sequenced to genotype the latent cellular replication competent HIV-1 in the initial sample. Methods of sequencing a nucleic acid molecule, such as a PCR amplicon, are well known in the art. Similarly, methods of detecting a mutation using allele-specific techniques are well known in the art. The disclosure is not limited to particular sequencing or allele-specific detection methods. HIV-1 genotyping methods of interest include, but are not limited to: the Trugene HIV-1 Genotyping Kit and Open Gene DNA Sequencing System (Siemens Medical Solutions Diagnostics Berkeley, Calif.); ViroSeq HIV-1 Genotyping System with the 3700 Genetic Analyzer (Celera Diagnostics Alameda, Calif.); and Versant HIV-1 RNA 3.0 (Siemens Medical Solutions Diagnostics Berkeley, Calif.).

Virus detection and quantification protocols may, in some instances, make use of controls or standards to verify that the detection assay has been appropriately performed (i.e., to serve as a positive control) and/or to provide a benchmark for quantification. For example, a separate control sample known to contain virus may be utilized as a positive control to determine that the assay is functional. A separate control sample known to contain a particular amount of virus may be utilized as a positive control and a measurement made from the control may be compared to a measurement from the test sample in order to allow quantification of the test sample. In some instances, a control may be an internal control, e.g., a known quantity of virus or other agent to be detected that is "spiked" into the test sample. Quantifying an internal control that has been added to the test sample before the assay may provide an internal standard which can be used to quantify the amount of host-derived virus present in the sample. Any convenient HIV standard may find use as a separate or internal control including e.g., the $3^{rd}$ HIV-1 International Standard available from the World Health Organization (NIBSC code: 10/152).

Standards used as controls may, upon detection, be indistinguishable or distinguishable from the measured analyte, e.g., viral RNA, provirus DNA, etc. For example, a spiked-in nucleic acid standard may be measured using amplification, hybridization, sequencing, etc. and the measured standard may be indistinguishable from the measured test analyte. In other instances, a spiked-in nucleic acid standard may be measured using amplification, hybridization, sequencing, etc. and the measured standard may be distinguishable from the measured test analyte. Any convenient method of making the nucleic standard distinguishable from the test analyte may be employed where distinguishing the standard from the test analyte is desirable, including e.g., employing a modified or mutant sequence for the standard, including a modified nucleic acid or nucleotide in the standard, etc. A modified or mutant sequence, when detected as a separate or internal control, allows the operator to distinguish a detected standard from a detected test analyte buy detecting the mutation or modification in the result. For example, in an amplification assay the amplification product of the modified or mutant standard may be a different size than expected of the test analyte or may contain sequence that is different than the test analyte. In hybridization based assays the modified or mutant standard may have different hybridization characteristics as compared to the test analyte. In sequencing based-assays, the modified or mutant standard may contain sequence that is different than that of the test analyte.

A standard, or a method of detecting a standard, may be configured to be both distinguishable from the test analyte while performing similarly to the test analyte in the detection or quantification assay. For example, a standard in an amplification based method may be configured such that the amplification product obtained from the standard is distinguishable from that of the test analyte but also be configured such that its amplification dynamics are essentially the same as the test analyte. In other cases, a method of detecting a standard in an amplification based method may be configured such that the amplification product obtained from the standard is distinguishable from that of the test analyte but also be configured such that its amplification dynamics are essentially the same as the test analyte. As a non-limiting example, in an amplification assay a standard may be employed that is amplified essentially the same as the test analyte but is detected by a standard-specific probe (e.g., as employed in the Roche COBAS® AmpliPrep/COBAS® TaqMan® HIV-1 Test).

In some instances, an evaluation of viral load may include the use of a virus stimulation positive control. Virus stimulation positive controls may vary depending on the particular stimulation method and the viral load measurement employed. Such virus stimulation positive controls will generally include a cell with an inducible viral element that predictably becomes activated upon contact with an effective amount of an HIV inducing agent. In some instances, a stable cell line with integrated provirus may find use as a virus stimulation positive control including but not limited to, e.g., the ACH-2 cell line. In many instances, a virus stimulation positive control does not express viral mRNA or expresses a low amount of viral mRNA in the absence of stimulation. Virus stimulation positive controls find use in a variety of purposes including but not limited to, e.g., verification of the functionality of a viral load assay, verification of the functionality of a stimulation method, etc.

Mutations in the HIV-1 protease (PR) and reverse transcriptase (RT) proteins are associated with HIV drug resistance (HIVDR), such as resistance to NNRTIs, NRTIs, and protease inhibitors. Thus, in one example genotyping HIV-1 permits detection of one or more HIV-1 PR or RT mutations known to be associated with drug resistance, or are newly identified as causing HIV-1 drug resistance.

In some examples, the methods can be used to select a therapy (i.e., determine a therapeutic regimen) for a patient infected with HIV-1. For example, if a patient is identified as not having an HIVDR mutation, then the patient can be treated with traditional AVTs, such as NNRTIs, NRTIs, and/or protease inhibitors (or whatever AVT is available). In a specific example, if a patient is identified as not having an HIVDR mutation, then the patient can be selected and treated with HAART. In contrast, if a patient is identified as having one or more HIVDR mutations, the patient is identified as one who will not benefit from particular ARTs. Mutations associated with particular resistance to a particular drug are known. Thus, if the subject is found to have an HIVDR associated with resistance to a particular drug, the patient should not be treated with that drug as their HIV-1 will be resistant and not treatable with that drug. A different therapy should be selected.

For example, if the patient is found to have one or more HIVDR mutations in the PR protein, the patient should not be treated with a protease inhibitor, such as amprenavir, indinavir, lopinavir, nelfinavir, ritonavir, saquinavir, or atazanavir (or at least not treated with the PR inhibitor associated with their HIVDR mutation). For example, a patient having the HIVDR PR mutation V82A/T/F/S should not be treated with indinavir or ritonavir, while a patient having the HIVDR PR mutation D30N should not be treated with nelfinavir. Instead, such patients could be treated with a RT inhibitor, such has an NNRTI or NRTI. Alternatively, such patients could be treated with other PR inhibitors; for example a patient having the HIVDR PR mutation D30N could be treated with lopinavir or ritonavir.

In contrast, if the subject is determined to have one or more HIV-1 RT mutations, then the patient will not benefit from RT inhibitor therapy and should not be treated with an RT inhibitor (or at least not treated with the RT inhibitor associated with their HIVDR mutation). For example, a patient having the HIVDR RT mutation K70R should not be treated with the NRTI zidovudine, while a patient having the HIVDR RT mutation K103N should not be treated with any NNRTI. Instead, such patients can be treated with protease inhibitors (such as one or more of amprenavir, indinavir, lopinavir, nelfinavir, ritonavir, saquinavir, and atazanavir). Alternatively, such patients could be treated with other RT inhibitors; for example a patient having the HIVDR RT mutation K103N could be treated with an NRTI.

If the patient is determined to have a combination of HIV-1 PR and RT mutations, then the patient will not benefit from protease inhibitor or RT inhibitor therapy (such as one that they are currently on). Instead, patients with one or more HIVDR mutations in both RT and PR can be treated with those ARVs for which are not associated with resistance due to the HIVDR mutation that patient has. For example a patient having the HIVDR PR mutation V32I the HIVDR RT mutation L74V could be treated with a nelfinavir and an NNRTI.

In some instances, the methods further include assessing the effectiveness of a HIV-1 therapeutic regimen based on the evaluation. For example, the assay may be performed at one or more time points following initiation of a therapeutic regimen in order to assess the effectiveness of that regimen. For a given regimen if, over time, the viral load decreases, including the viral load attributable to latent cellular virus, then the therapeutic regimen may be viewed as effective. In contrast, if no decrease in viral load or an increase in viral load is observed, then the therapeutic regimen may be viewed as ineffective, where in such instances a new therapeutic regimen may be identified and employed.

In some instances, the method further includes obtaining the cellular sample from a living subject. The cellular sample may be obtained using any convenient protocol, e.g., using any convenient blood draw protocol.

In some embodiments, the methods involve evaluating a sample originating from a subject known to be infected with HIV. As such, methods described herein involve evaluating an HIV infected cellular sample where the sample is obtained from a subject known to be infected with HIV. A subject known to be infected with HIV, and a sample there from, may be but is not limited to a subject having had at least one positive HIV test, a subject having been diagnosed with an HIV infection by a clinician, etc.

HIV infected samples may be obtained from HIV infected subjects at any period during the course of infection. For example, a sample may be obtained within hours following infection, within hours or days following diagnosis, during primary infection (i.e., acute infection), during clinical latency, during clinical disease (i.e. during clinically apparent disease), before treatment, during treatment, following treatment, between rounds of treatment, after a course of treatment, etc. Stages of HIV progression are well-known and described in e.g., Coffin et al. *Retroviruses*. Cold Spring Harbor (N.Y.): Cold Spring Harbor Laboratory Press, 1997; the disclosure of which is incorporated herein by reference in its entirety. In many embodiments, methods for evaluating a sample for latent cellular replication competent HIV will be performed in a sample collected during latent infection, before, during and/or after treatment for HIV, and/or at other times during an HIV infection when latent virus is suspected to be present. Although variable, latent infection occurs in many HIV infected subjects about four to six weeks after the appearance of symptoms of the initial acute phase and subjects in the latent period are generally asymptomatic and have low level viremia.

Multiple HIV genotypes may be present in a subject at a time and/or through the course of the disease either by mutation of an HIV genome already present in the subject or through primary infections with more than one genotype. The genotype of latent cellular replication competent HIV may be determined, e.g., in instances where subjects are infected with multiple genotypes. HIV genotyping may be performed in a cellular sample from the subject prior to and following stimulation where the genotype(s) with the greatest increase in viral load following stimulation have an increased likelihood of being latent cellular replication competent HIV genotypes. In some instances, identification of a particular latent cellular replication competent HIV genotype in a subject may be used to determine (e.g., modify or maintain) an effective treatment protocol for the subject. For example, identification of a latent cellular replication competent genotype containing a drug resistant HIV mutation may lead to selection of a particular therapy and administration of a particular drug based on the identified latent genotype containing a resistance mutation.

In some instances, the viral loads of latent cellular replication competent viral genotypes and non-latent viral genotypes are compared, where "non-latent" virus refers to virus that is present in the absence of stimulation at a level above that of latent cellular replication competent virus. The viral load may be determined for a plurality of viral genotypes, including each viral genotype of a subject, before and after stimulation and the viral loads may be compared. Whether a viral genotype is a latent or non-latent virus may be determined based on the comparison, where an increase in viral load indicates a latent cellular replication competent virus and a lack of an increase indicates a non-latent virus and/or a replication incompetent virus. In some instances, relative comparisons may be performed, e.g., the viral load of genotype X may be compared relative to the viral load of genotype Y both before and after stimulation. A treatment protocol may be selected based on identification of a viral genotype as either latent or non-latent and replication competent or non-replication competent and a particular HIV treatment, e.g., administration of a particular HIV drug, may be administered to a subject based on the identification.

In evaluating an increase in viral load following stimulation as, described herein, any convenient and appropriate threshold may be used to identify those samples that are likely to contain latent cellular replication competent virus depending on the particular assay employed. Stimulation may be evaluated, i.e., to detect an increase, in any convenient way including but not limited to, e.g., comparison of measurements performed on the same sample before and after stimulation, comparison of measurements performed on a stimulated sample and a non-stimulated control, etc. For example, a sample may be indicated as containing latent cellular replication competent virus when a greater than 0.5 log increase is seen in viral load following stimulation. In some instances, changes in viral load may be expressed in terms of fold-change and the presence of latent cellular replication competent virus may be indicated when a greater than 2-fold increase in viral load is measured where the threshold cut-off will vary and may range from 2-fold to 50-fold or more including but not limited to, e.g., a greater than 3-fold increase, a greater than 4-fold increase, a greater than 5-fold increase, a greater than 6-fold increase, a greater than 7-fold increase, a greater than 8-fold increase, a greater than 9-fold increase, a greater than 10-fold increase, a greater than 11-fold increase, a greater than 12-fold increase, a greater than 13-fold increase, a greater than 14-fold increase, a greater than 15-fold increase, a greater than 20-fold increase, a greater than 25-fold increase, a greater than 30-fold increase, a greater than 35-fold increase, a greater than 40-fold increase, etc. Where an increase above a predetermined threshold is observed, the subject from which the sample is derived may be said to be infected with latent replication competent HIV or to have an increased likelihood of being infected with latent replication competent HIV, where the confidence in the determination may be based on the particular threshold used and/or the degree of the observed increase.

Cellular Sample Collection Containers

An aspect of the present disclosure includes a container for processing a sample, such as a whole blood sample. Containers as described herein are useful for performing methods such as described above.

Containers of interest may be fabricated from any convenient material. The container can be made of glass, plastic or other suitable materials. Plastic materials can be oxygen impermeable materials or contain an oxygen impermeable layer. Transparent materials are of interest, such as transparent thermoplastic materials like polycarbonates, polyethylene, polypropylene, polyethylene-terephtalate. The container also has a suitable dimension selected according to the required volume of the biological sample being collected. In one embodiment, containers have a tubular shape with an axial length of 60-mm to 130-mm and a diameter of 10-mm to 20-mm. A container that is a tube having an axial length ranging from 75-mm and 100-mm millimeters and a diameter ranging 13-mm to 16-mm are is of interest.

The containers may include a closure material over an otherwise opening of the container material. In some instances, the closure member is made of a resilient material to provide a seal for retaining the sample in the container. Of interest is a closure made of a resilient material capable of maintaining an internal pressure differential less than atmospheric and that can be pierced by a needle to introduce a biological sample into the container. Suitable materials for closure include, for example, silicone rubber, natural rubber, styrene butadiene rubber, ethylene-propylene copolymers and polychloroprene. Thus in certain embodiments, the closure member is a septum pierceable by a cannula. The closure may also provide convenient access to a biological sample within the container, as well as a protective shield that overlies the closure. As such, the closure may further include a removable cover, such as a threaded or snap-on cap or other suitable member that can be applied over the outside of the closure for various purposes. For instance, a threaded cap can be screwed over the closure after the sample collection to provide a second seal and further increase user safety. Any component of the device can be color coded, labeled, or otherwise tagged or marked for easy identification.

The device as assembled can be provided to maintain an internal pressure differential between atmospheric pressure outside of the container and is at a pressure less than atmospheric pressure. The pressure can be selected to draw a predetermined volume of a biological sample. In some instances, the biological sample is drawn into the first chamber by piercing a closure comprising a resilient material with a needle or cannula, such as is typical for known evacuated sample containers for drawing blood. An example of a suitable containers and closures are disclosed in U.S. Pat. No. 5,860,937, which reference is incorporated in its entirety. One aspect of interest is where the internal pressure of the container is selected to draw a predetermined volume of about 2.0 ml to about 10 ml of biological sample into the first chamber, and more particularly, about 2.5 ml to about 5 ml into the first chamber of the device.

As such, containers of interest may enclose an evacuated interior volume having a HIV-1 inducing agent, e.g., described above, present therein. In certain embodiments, the container may have an elongated shape where the length of the container is greater than a cross-section of an opening of the container. Embodiments of containers of interest include containers shaped in a form of a tube. The tube may have flat bottom, conical bottom, or a rounded bottom. In certain cases, the container may enclose an evacuated interior volume defined by a bottom wall and a side wall, the side wall further defining an open end. The volume of the container may vary as desired, and in some instances ranges from 1 to 1000 ml, such as 5 to 500 ml, e.g., 5 to 100 ml, including 5 to 50 ml. The open end or ends of the container may be sealed with a sealing elements, as desired, such as by a septum, e.g., where an opening is covered by a puncturable septum.

As noted above, a HIV-1 inducing agent may be disposed inside the container. In certain embodiments, the HIV-1 inducing agent may be coated on the interior surface, e.g., a bottom wall and/or a side wall, of the container. In some embodiments, the coating of the HIV-1 inducing agent is dried on the interior surface of the container. In some cases, the HIV-1 inducing agent is stably associated, e.g., covalenty attached, to an interior wall of the container.

The HIV-1 inducing agent may be disposed in the evacuated container and may be stably associated with a solid support, where the solid surface is an interior surface of the container or a bead disposed inside the container. For example, the HIV-1 inducing agent may be covalently attached to a bead, e.g., latex, agarose, sepharose, streptavidin, tosylactivated, epoxy, or carboxyl beads.

In certain cases, the HIV-1 inducing agent may be disposed in the container in a liquid form. The container may be provided with the HIV-1 inducing agent in a liquid or the liquid may be subsequently dried and the container may be provided with the HIV-1 inducing agent in a dried form, e.g., lyophilized form.

In certain cases, the container may include additives to improve stability of the HIV-1 inducing agent, such as, buffers, glycerol, phenylmethanesulfonyl fluoride (PMSF). Additional additives may also be present in the container, such as, additives that preserve the cells present in whole blood, e.g., platelet stabilizing factor, and the like. Exemplary additives that may be included in the container are anticoagulants such as ethylenediaminetetraacetic acid (EDTA), buffered citrate, or heparin. The container may include these additives in a liquid or dried state.

In certain cases, the container may be coded to facilitate identification and/or tracking of the container. Any component of the container can be color coded, labeled, or otherwise tagged or marked for easy identification.

As noted above, in some instances the container is evacuated, i.e., the interior of the container is at a pressure less than atmospheric pressure. The pressure may be selected to draw a predetermined volume of a whole blood sample. For example, the container may draw a whole blood sample of 1 ml-20 ml, e.g., 2 ml-10 ml, such as, 2 ml, 3 ml, 4 ml, 5 ml, 6 ml, 7 ml, 8 ml, 9 ml, or 10 ml.

In some instances, the sample is drawn into the container by piercing the septum with a needle or cannula, such as is typical for known evacuated sample containers for drawing blood. Examples of suitable containers and closures are disclosed in U.S. Pat. Nos. 5,860,937; 5,344,611; 5,326,535; 5,320,812; 5,257,633 and 5,246,666, each of which is incorporated by reference here in its entirety.

Utility

The subject methods, devices, and systems find use in a variety of different applications. For example, the methods, devices and systems find use in diagnosing and treating individuals suffering from HIV-1 infection. The methods, devices and systems also find use in providing a prognosis for a subject already known to be infected with HIV and undergoing treatment for HIV.

In addition, the methods, devices and systems find use in evaluating treatment protocols for individual patients based on the presence or absence of latent cellular replication competent viral infection. The methods, devices and systems also find use in evaluating a subject to identify the genotype of a latent cellular replication competent virus and/or identify the presence or absence of a viral mutation in a latent virus. In particular, the subject methods, devices and systems allow for determining if a subject has a latent cellular replication competent HIV infection and/or what viral genotype comprises the latent infection without administering to the subject an agent that stimulates the virus.

In some instances, preferentially measuring virus produced following stimulation of the cells, e.g., by excluding cell-free virus present before stimulation, allows for identification of the primary pathogenic replication competent HIV genotype present in a subject. Without being bound by theory, the dominate cell-free HIV genotype prior to stimulation may not be representative of the integrated replication competent provirus that is contributing or will primarily contribute to clinical progression, particularly as the cell-free virus may contain mutations or other genetic differences that are not present in the provirus and viral genomes generated from the provirus. As described herein, determining the HIV genotype of virus produced following stimulation provides significant clinical benefits including enabling a medical practitioner to tailor a treatment protocol or drug cocktail to a subject's particular HIV infection and/or avoid particular treatments or HIV drugs to which a subject may harbor resistance.

The methods, devices, and systems described herein find use in identifying HIV cellular reservoirs and thus improve therapeutic approaches aimed at HIV eradication. Furthermore, the subject methods, devices, and systems may be utilized in HIV patient screening to identify those patients which contain or are unlikely to contain latent replication competent HIV. Such screening allows the medical practitioner to better match an HIV patient with an effective therapy. In addition, screening for latent replication competent HIV genotypes that contain a drug resistance marker provides the medical practitioner with an additional tool to avoid administering a drug to an HIV patient to which that patient is likely to be resistant.

Kits

In another aspect, provided herein are kits for practicing the subject methods, e.g., as described above. Kits may include an HIV-1 inducing agent, which may be present in or provided along with a sample collection container, e.g. as described above. Kits may further include a means or device for controlling the temperature of a sample collection container following collection of the sample. For example, a kit may include a temperature controlling device configured to maintain a low temperature for sample storage and/or transport where a low temperature may be any temperature where cellular activities, including viral replication and/or activation, is inhibited including but not limited to e.g., less than 10° C., less than 4° C., less than 0° C., less than −10° C., less than −20° C., etc. In other instances, a kit may include a temperature controlling device configured to maintain an elevated temperature for incubation of the sample where an elevated temperature generally refers to a temperature above ambient or room temperature and may be but is not limited to any incubation temperature as described herein.

Subject kits may further include one or more control reagents useful in performing the methods and evaluating sample comparisons as described herein. Control reagents included in the described kits include but are not limited to virus standards, HIV infected cells and/or cell lines, control probes, control primers, etc.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, flash drive, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

I. Materials and Methods

A. Blood Collection

For each subject, whole blood is collected into one of three HIV-1 activation tubes containing PHA (ViraStim tubes, IncellDx, Inc Menlo Park, Calif.), and one EDTA tube. After collection, the tubes are shaken vigorously for 5 seconds to ensure that the entire inner surface of the tubes are coated with blood.

The EDTA tube is centrifuged for plasma collection by spinning the tube at 2500 RCF (g) for 30 minutes at room temperature (15-30° C.), upon receipt of blood collection tube, and within 24 hours of collection. The gel plug that separates the cells from the plasma by density is employed fractionate the blood sample. The three HIV-1 activation tubes are transferred to a 37° C. incubator as soon as possible, and within 24 hours of collection. The tubes are mixed again, prior to incubation, as described above. The blood samples are not refrigerated or frozen prior to plasma isolation.

The ViraStim tubes are then incubated upright at 37° C. for the following times periods:

ViraStim tube 1: 24±1 hours.
ViraStim tube 2: 48±2 hours.
ViraStim tube 3: 72±3 hours.

After incubation of the tubes at 37° C., plasma is collected by centrifuging the tubes for 30 minutes at 2500 RCF (g), at room temperature (15-30° C.). A gel plug present in the ViraStim tubes will separate the cells from the plasma. If this does not occur, the tubes are centrifuged again at a higher speed.

Plasma samples are collected, stored at ≤−20° C. (for up to 2 weeks) and the viral load in the plasma is measured using the Roche COBAS® AmpliPrep/COBAS® TaqMan® HIV-1 Test.

B. Plasma Viral Load

Plasma samples are collected, stored at ≤−20° C. (for up to 2 weeks) and the viral load in the plasma is measured using the Roche COBAS® AmpliPrep/COBAS® TaqMan® HIV-1 Test with a lower limit of detection of <20 copies per mL of plasma.

C. HIV-1 Reservoir Quantification Using Simultaneous Ultrasensitive Subpopulation Staining/Hybridization In Situ (SUSHI)

The SUSHI protocol has been described in detail previously. Known significant cellular reservoirs were selected for this analyses and further delineated into memory and naïve T cells in resting and activated states, and monocyte to macroViraStimge differentiation to discern relative levels of gag-pol+ reservoirs (Table 1). SUSHI reagents 1 through 7 are available from IncellDx (Menlo Park, Calif.). Fresh PBMCs isolated from whole blood are washed and re-suspended in PBS, pH 7.4 containing 2% FBS to a final concentration of $1\times10^7$ cells/mL and 100 µl ($1\times10^6$ PBMCs) are transferred to a 12×75 mm Falcon tube (Becton, Dickinson and Company, Bedford, Mass., U.S.A.). An appropriate dilution of antibodies (Becton Dickinson, San Jose, Calif. or BD ViraStimrmigen San Diego, Calif., U.S.A.), Table 1, in pre-determined combinations is added to the cell suspension and incubated at room temperature for 30 minutes. Cells are washed in 1 ml PBS+2% FBS, pH 7.4 and centrifuged at 600×g for 5 min at room temperature. The supernatant is aspirated and cells are re-suspended and fixed in 1 mL Reagent 1 and incubated at room temperature for 1 hour. Following incubation, the fixed cells are washed in 1 mL Reagent 2 (prehybridization buffer 1), inverted gently, and centrifuged at 600×g for 5 min at room temperature. The supernatant is aspirated followed by the addition of 1 mL Reagent 3 (prehybridization buffer 2), inverted gently, and centrifuged at 600×g for 5 min at room temperature. The supernatant is aspirated followed by the addition of 100 µL Reagent 4 (hybridization buffer) and 3 µL Reagent 5 (HIV-1 probe cocktail) and incubated in a 43° C. water bath for 30 minutes. Following incubation 1 mL of pre-warmed (43° C.) Reagent 6 (stringency wash 1) is added, the tube inverted gently and centrifuged at 600×g for 5 min at room temperature. The supernatant is aspirated, the cell pellet gently re-suspended in the residual fluid followed by the addition of 1 ml pre-warmed (43° C.) Reagent 7 (stringency wash 2) and incubated in a 43° C. water bath for 15 min. The tube is centrifuged at 600×g for 5 min at room temperature, the supernatant aspirated, the cell pellet gently re-suspended in the residual fluid followed by the addition 200 µL of 1×PBS, pH 7.4. Samples are then collected and analyzed on the i-Cyt EC800 (Sony Biotechnology, Champaign, Ill.).

D. HIV+ and HIV− Controls.

The ACH-2 cell line containing a single copy of integrated HIV-1 proviral DNA per cell with limited to no expression of HIV-1 mRNA is routinely used as a control and residual HIV-1 mRNA is not detected with the SUSHI gag-pol probes (below level of detection). Induction of ACH-2 HIV-1 RNA expression with phorbol 12-myristate 13-acetate (PMA) at 80 µg/mL PMA (Sigma Aldrich, St. Louis, Mo., U.S.A) is used as a positive control to verify hybridization and signal detection of SUSHI gag-pol probes. This cell line is used as a positive (stimulated) and an operationally negative (unstimulated) control in the first publication describing the SUSHI technology demonstrating a linear response between the percentage of stimulated ACH-2 cells as measured by the SUSHI fluorescent HIV-1 gag-pol probes versus actual percentage of stimulated ACH-2 cells by dilution.

E. HIV-1 Reservoir Sequencing

HIV-1 Reservoir sequencing was conducted by TRU-GENE HIV-1 Genotyping kit.

II. Results

A. Quantification of Replication-Competent HIV-1

Figure 1A:
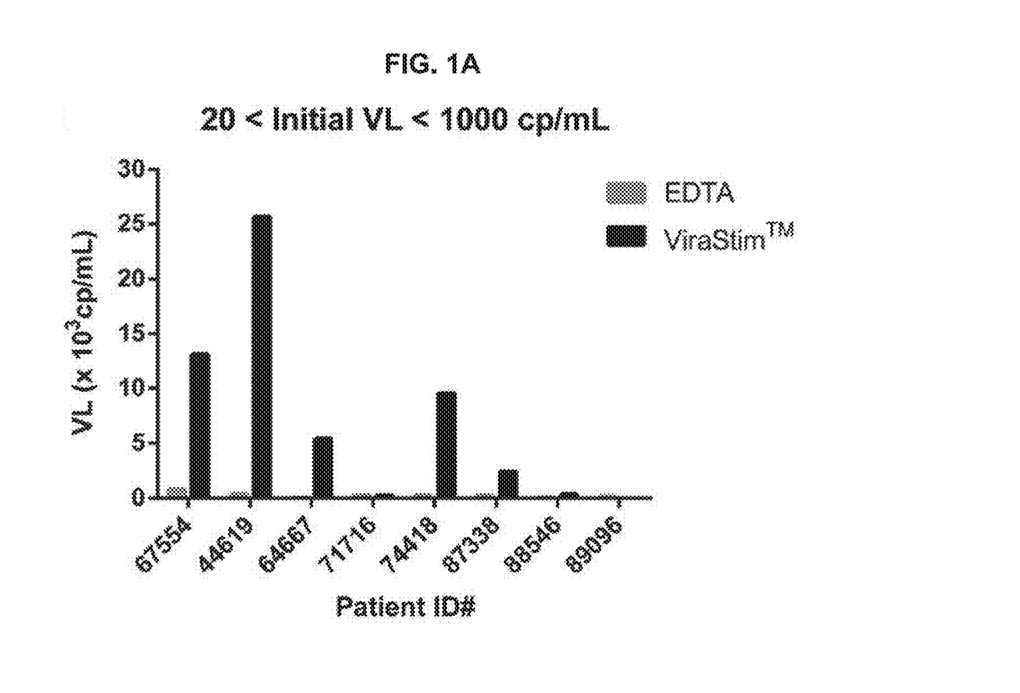
FIGS. 1A, 1B and 2 provide results of viral load determination in PHA and EDTA tubes, as described in the Experimental Section, below.
Figure 1B:
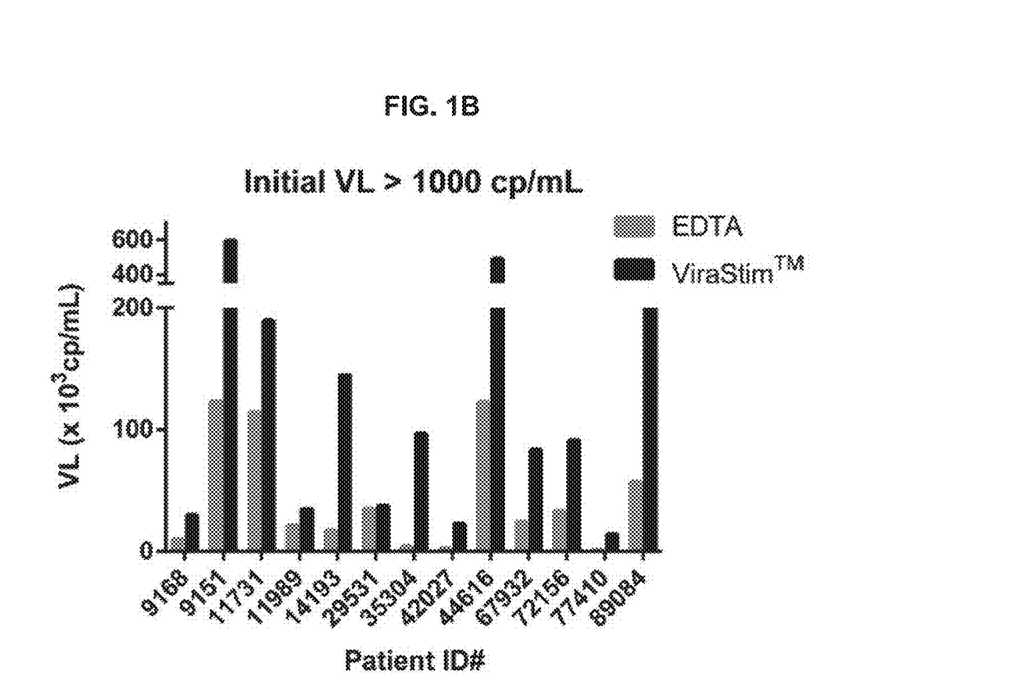
Figure 2:
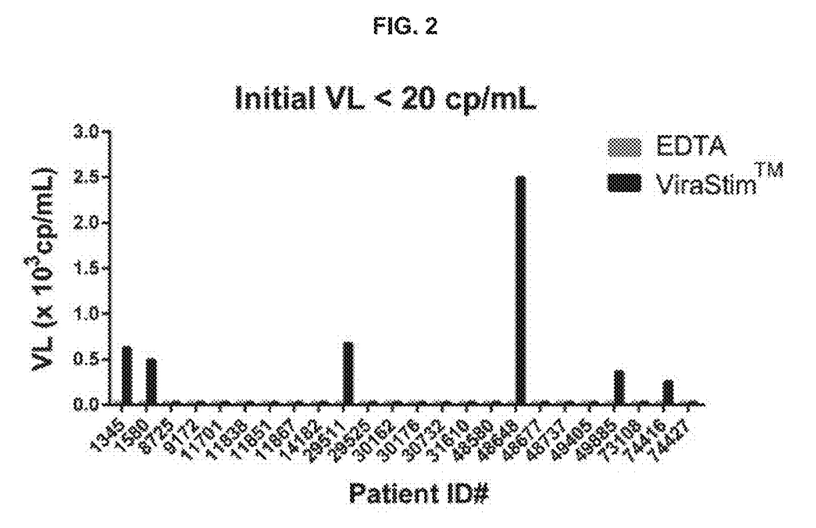

To determine the relative amounts of replication competent HIV-1 in hematopoietic cells in peripheral blood, we used specialized blood collection tubes ((VIRASTIM tubes) containing the HIV-1 inducing compound phytohemagglutinin. By collecting blood plasma from EDTA tubes as a control and heparin anti-coagulated, VIRASTIM-containing tubes, we quantified plasma viral load. The difference between plasma viral load in EDTA tubes and plasma viral load in VIRASTIM tubes incubated for 48 hours at 37 degrees represents the amount of replication competent virus residing in cells contained within the blood sample. As demonstrated in FIGS. 1A, 1B and 2, replication competent virus was induced to replicate independent of the plasma viral load. The percentage of patients with replication competent virus in PBMCS varies depending on the baseline plasma viral load in the EDTA tubes. Six out of ten patients with starting plasma viral load <20 copies/mL (cp/mL), six out of eight patients with starting viral loads >20 and <1000 cp/mL, and eight patients out of thirteen with starting viral loads >1000 all showed an increase greater than 0.5 log.

B. Identification of Replication Competent HIV-1 Reservoirs

Figure 4:
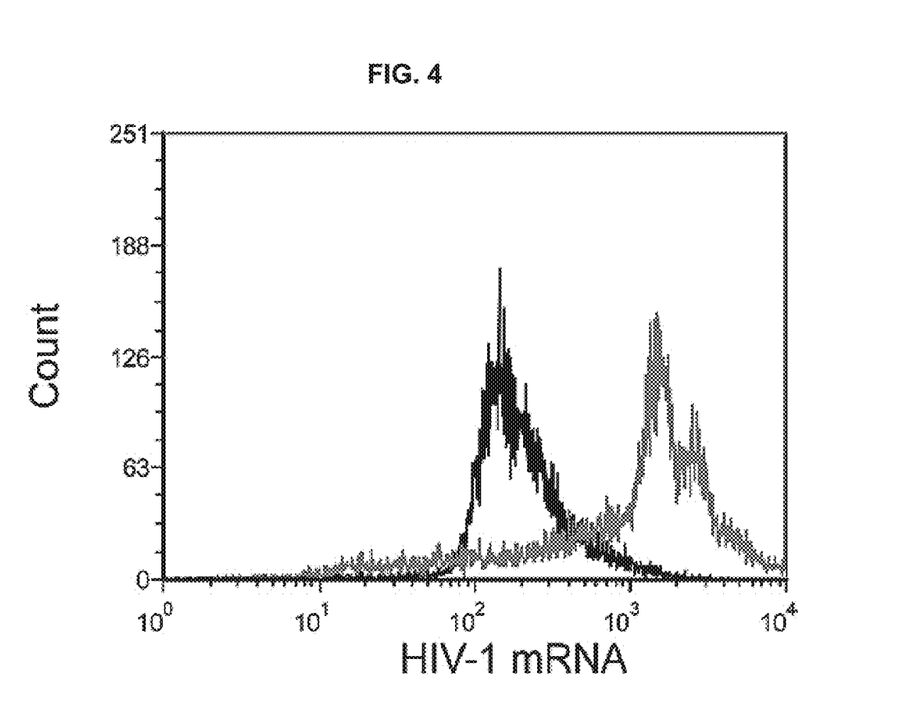
FIG. 4 provides histograms confirming functionality of the SUSHI assay and the specificity of viral stimulation, as described in the Experimental Section, below.
Figure 5:
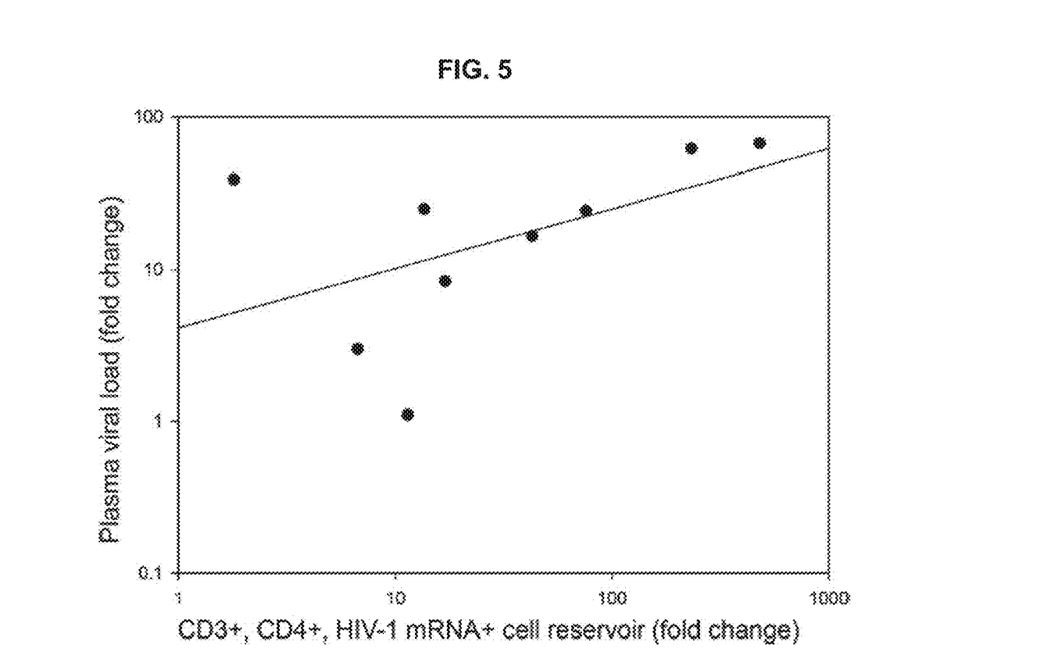
FIG. 5 demonstrates the correlation between changes in plasma viral load and cellular viral load in PBMCs attributed to stimulation with ViraStim tubes as described in the Experimental Section, below.

To confirm the results seen in viral activation tubes and to identify the reservoirs of HIV-1 in PBMCS harboring replication competent virus, we performed SUSHI on cells in paired EDTA and ViraStim tubes and compared the percentage of cells with replicating HIV-1 as between the two tubes. Hybridization performance of the SUSHI assay is shown in FIG. 4, where HIV-1 mRNA was measured in control stimulated (right histogram) and unstimulated (left histogram) ACH-2 cells confirming the performance of the assay and the specificity of HIV stimulation. As demonstrated in FIG. 5, increased HIV-1 replication in CD3+CD4+ T lymphocytes as determined by SUSHI confirmed the source of increased virus seen in the viral activation tubes. In particular the extent of viral load increase was proportional to the fold increases in cells containing replicating virus.

C. Assessment of HIV-1 Quasi-Species Specific Genotypic Resistance Patterns

Figure 3:
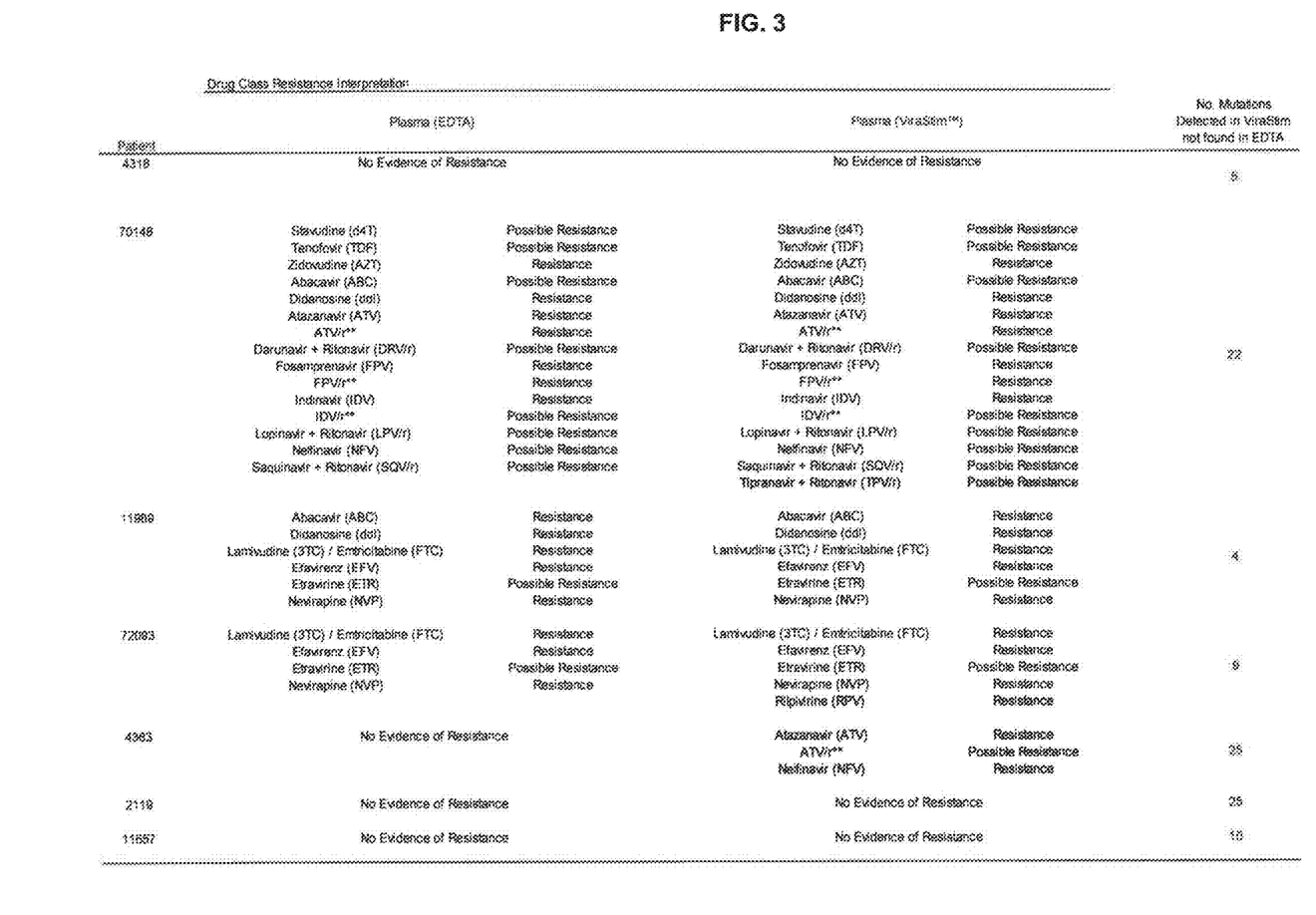
FIG. 3 provides a summary of genotypic variation as identified from PHA and EDTA tubes, as described in the Experimental Section, below.

Since HIV-1 virus contained in plasma represents only a single viral reservoir in HIV-1 infected individuals and since this reservoir is the only reservoir routinely assessed during anti-retroviral resistance testing, we used plasma virus collected in ViraStim tubes to compare resistance genotypes in plasma to resistance phenotypes in virus derived from PBMCS and plasma. As shown in FIG. 3, 4 out of 7 patients demonstrated additional genotypic resistance determinants in ViraStim tubes compared to EDTA tubes.

III. Discussion

With the HIV field moving toward eradication strategies, elucidation and monitoring of HIV-1-infected reservoirs is critical. To that end, we performed studies aimed at combining analyses of replication competent HIV-1 reservoirs with the virus already present in plasma to obtain a broader representation of HIV-1 quasi-species.

VIRASTIM stimulation on whole blood resulted in a >0.5 log increase in plasma viral load in samples obtained from patients, as compared to viral load measured in EDTA tubes. This cut-off of >0.5 was chosen since it is greater than what would be expected from the intra-run variability of viral load assays. Though many approaches and many publications have demonstrated the ability to stimulate viral replication from PBMCS in in vitro cultures, this is the first report of a clinical approach to stimulate viral replication in a clinical sample prior to common clinical diagnostics.

To further confirm that the increase in viral production was a result of stimulating latent, replication competent virus, we performed SUSHI analysis on HIV-1 reservoirs (e.g., CD3, CD4 T-cells). We demonstrated a correlation between the fold increase in HIV replication in intact cells and the fold increase in the ViraStim tubes relative to the EDTA tubes. We have previously shown the utility of SUSHI in measuring decreases in viral replication associated with anti-retroviral therapy and in the present study we demonstrate utility in the detection of increased viral replication, which is useful in the monitoring of eradication strategies.

As additional evidence that the increase in viral replication seen in ViraStim tubes reflects a broader quasi-species representation than in the sample tube, we found differences in resistance mutations and amino acid changes when compared to an EDTA control. This shows that the viral phenotypes detected by sequencing out of plasma are not fully representative of the viral quasi-species in cellular reservoirs. Plasma contains a mixture of both replication competent and replication defective virus. HIV phenotyping is typically performed on the mixture of the two cloned into replication competent backgrounds providing a resistance profile that is skewed by the non-functional virus particles. In addition, virus that is latent and currently unexpressed is not represented in normal plasma. "It has been shown that a cessation of HAART treatment or a switch in antiretroviral drugs in patients treated for more than two years with suboptimal drug regimens result in a replacement of the resistant virus in the plasma by wild-type variants. In the majority of the patients studied, the replacement of the mutant by the wild-type virus was abrupt and fast, indicating that it was the result of the reappearance of archived wild-type virus and not of the reversal of mutations in the resistant variants. If wild-type virus persists in the latent reservoir for such a long time, then it could be postulated that drug-resistant strains too will be conserved." (Journal of Antimicrobial Chemotherapy (2005) 55, 410-412 Noe et al.)

However, all of these plasma-based measurements on isolated nucleic acids yield no information on the cell types and subpopulations that are productively infected and, thus, are contributing to the free virus pool in the plasma. To look into the source of the increase in virus and the change in resistance profiles, we looked at the cellular reservoirs and measured mRNA expression of lymphocyte subsets. Since replication competent CA HIV-1 reservoirs stand in opposition to HIV eradication, new strategies have been employed to reactivate these reservoirs using compounds such as histone deacetylase inhibitors (HDACs) among others. The approach presented in this paper can be used to pre-screen patients who would respond best given that the ViraStim tubes demonstrate the degree of stimulation to be expected at least in the PBMC reservoir which, as previously mentioned, reflects the total tissue reservoir of HIV. Further the ART backbone used in patients induced by HDAC could be tailored based on sequencing data on the induced PBMC reservoir as described in the present study.

IV. Summary

Though effective for monitoring, plasma viral load and CD4 counts do not give a full representation of viral quasi-species in cellular reservoirs, the major repository of replication competent HIV-1 in infected individuals. To that end, we sought to develop a diagnostic system that could stimulate the replication competent HIV-1 reservoirs and improve selection of anti-retroviral regimens. Whole blood from HIV infected individuals was collected into one ViraStim™ HIV-1 activation tube and one EDTA tube. Plasma samples were then tested for viral load and cell-type specific HIV-1 replication. Further, seven matched activated/non-activated samples were sequenced using TRUGENE® HIV-1 Genotyping Kit. The percentage of patients with replication competent virus in PBMCs varied depending on the baseline plasma viral load in the EDTA tubes. Six out of ten patients with starting plasma viral load<20 copies/mL (cp/mL), six out of eight patients with starting viral loads >20 and <1000 cp/mL, and eight patients out of thirteen with starting viral loads >1000 all showed an increase greater than 0.5 log. We confirmed that this increase came from cellular reservoirs in blood using Simultaneous Ultrasensitive Subpopulation Staining/Hybridization In Situ (SUSHI). When comparing resistance genotypes in plasma from activation tubes compared to EDTA tubes for seven patients, all patients showed additional mutations in the activation tube while three patients demonstrated additional genotypic resistance determinants compared to EDTA tubes. This study shows that HIV-1 viral replication can be stimulated directly from infected whole blood. The sequencing results showed 3 of 7 cases demonstrated additional drug resistance following stimulation which has the potential to more accurately identify anti-retroviral resistance.

Notwithstanding the appended clauses, the disclosure set forth herein is also defined by the following clauses:

1. A method of evaluating a cellular sample for latent cellular replication competent HIV-1, the method comprising:
    contacting a cellular sample with an HIV-1 inducing compound to produce an activated cellular sample; and
    assessing plasma viral load in the activated cellular sample to evaluate the cellular sample for latent cellular replication competent HIV-1.
2. The method according to Clause 1, wherein the cellular sample comprises a blood sample.

3. The method according to Clause 2, wherein the blood sample is a whole blood sample.
4. The method according to Clauses 2 or 3, wherein the evaluating comprises evaluating latent cellular replication competent HIV-1 from PBMCs.
5. The method according to any of Clauses 1 to 4, wherein the evaluating comprises determining the presence of latent cellular replication competent HIV-1.
6. The method according to Clause 5, wherein the determining is a qualitative determination.
7. The method according to Clause 5, wherein the determining is a quantitative determination.
8. The method according to any of the preceding clauses, wherein the HIV inducing compound comprises a lectin.
9. The method according to Clause 8, wherein the lectin comprises a phytohemagglutinin.
10. The method according to any of the preceding clauses, wherein assessing plasma viral load comprises employing a nucleic acid mediated protocol.
11. The method according to Clause 10, wherein the nucleic acid mediated protocol comprises a real-time PCR protocol.
12. The method according to any of the preceding clauses, wherein the method further comprises genotyping identified latent cellular replication competent HIV-1.
13. The method according to any of the preceding clauses, wherein the method further comprises producing a HIV-1 therapeutic regimen based on the evaluation.
14. The method according to any of Clauses 1 to 13, wherein the method further comprises assessing the effectiveness of a HIV-1 therapeutic regimen based on the evaluation.
15. The method according to any of the preceding clauses, wherein the method further comprises obtaining the cellular sample from a living subject.
16. The method according to Clause 15, wherein the living subject is a human.
17. A cellular sample collection container comprising:
    an anti-coagulant; and
    a HIV-1 stimulating agent.
18. The cellular sample collection container according to Clause 17, wherein the anti-coagulant comprises heparin.
19. The cellular sample collection container according to Clauses 17 and 18, wherein the HIV-1 stimulating agent comprises a lectin.
20. The cellular sample collection container according to Clause 19, wherein the lectin comprises a phytohemagglutinin.
21. The cellular sample collection container according to any of Clauses 17 to 20, wherein container is a tube.
22. The cellular sample collection container according to any of Clauses 17 to 21, wherein the container encloses an evacuated interior volume and comprises an opening sealed by a septum.
23. A kit comprising:
    a cellular sample collection container according to any of Clauses 17 to 22; and
    a plasma viral load detection system.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions.

Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of evaluating a cellular sample for latent cellular replication competent HIV-1, the method comprising:
    activating a whole blood sample, the activating consisting essentially of contacting the whole blood sample with an HIV-1 inducing compound consisting essentially of a lectin to produce an activated cellular sample, wherein the whole blood sample is not contacted with culture medium; and
    assessing plasma viral load in the activated cellular sample to evaluate the cellular sample for latent cellular replication competent HIV-1.
2. The method according to claim 1, wherein the evaluating comprises evaluating latent cellular replication competent HIV-1 from PBMCs.
3. The method according to claim 1, wherein the evaluating comprises determining the presence of latent cellular replication competent HIV-1.
4. The method according to claim 1, wherein the lectin comprises a phytohemagglutinin.
5. The method according to claim 1, wherein assessing plasma viral load comprises employing a nucleic acid mediated protocol.
6. The method according to claim 5, wherein the nucleic acid mediated protocol comprises a real-time PCR protocol.
7. The method according to claim 1, wherein the method further comprises genotyping identified latent cellular replication competent HIV-1.
8. The method according to claim 1, wherein the method further comprises producing a HIV-1 therapeutic regimen based on the evaluation.
9. The method according to claim 1, wherein the method further comprises assessing the effectiveness of a HIV-1 therapeutic regimen based on the evaluation.
10. The method according to claim 1, wherein the method further comprises obtaining the cellular sample from a living subject.
11. The method according to claim 1, wherein the contacting consists essentially of placing the blood sample into a container comprising the HIV-1 inducing compound.
12. The method according to claim 11, wherein the HIV-1 inducing compound is coated on an interior surface of the container.
13. The method according to claim 11, wherein the blood sample is collected from a living subject into the container.

14. The method according to claim 1, wherein the HIV-1 inducing compound consists of a lectin.

15. The method according to claim 14, wherein the lectin is phytohemagglutinin.

16. The method according to claim 1, wherein the activating consists of contacting the whole blood sample with the HIV-1 inducing compound.

17. The method according to claim 1, wherein the activating comprises incubating the whole blood sample with the HIV-1 inducing compound for a period of 12 hours to 96 hours to produce the activated cellular sample.

18. The method according to claim 17, wherein the period is 24 hours to 72 hours.

19. The method according to claim 4, wherein assessing plasma viral load comprises employing a nucleic acid mediated protocol.

20. The method according to claim 19, wherein the activating comprises incubating the whole blood sample with the HIV-1 inducing compound for a period of 24 hours to 72 hours to produce the activated cellular sample.

21. The method according to claim 20, wherein the nucleic acid mediated protocol comprises a real-time PCR protocol.

\* \* \* \* \*

UNITED STATES PATENT AND TRADEMARK OFFICE
CERTIFICATE OF CORRECTION

PATENT NO. : 10,308,990 B2  
APPLICATION NO. : 14/807817  
DATED : June 4, 2019  
INVENTOR(S) : Bruce K. Patterson et al.

Page 1 of 1

It is certified that error appears in the above-identified patent and that said Letters Patent is hereby corrected as shown below:

On the Title Page

Under item (54), please correct the title so that it reads:
"(54) METHODS OF EVALUATING A CELLULAR SAMPLE FOR LATENT CELLULAR REPLICATION COMPETENT HIV-1, AND COMPOSITIONS AND KITS FOR USE IN PRACTICING THE SAME"

Under item (71), please correct the Applicant's address so that it reads:
"(71) Applicant: IncellDx, Inc., San Carlos, CA (US)"

Signed and Sealed this
Seventeenth Day of September, 2019

Andrei Iancu
*Director of the United States Patent and Trademark Office*